(12) United States Patent
Kollar

(10) Patent No.: US 8,580,282 B2
(45) Date of Patent: Nov. 12, 2013

(54) DENTAL ANESTHETIC COMPRISING TETRACAINE AND A VASOCONSTRICTOR FOR INTRANASAL ADMINISTRATION

(75) Inventor: Mark David Kollar, Fort Collins, CO (US)

(73) Assignee: St. Renatus, LLC, Fort Collins, CO (US)

( * ) Notice: Subject to any disclaimer, the term of this patent is extended or adjusted under 35 U.S.C. 154(b) by 0 days.

(21) Appl. No.: 13/262,704

(22) PCT Filed: Apr. 2, 2010

(86) PCT No.: PCT/US2010/001002
§ 371 (c)(1),
(2), (4) Date: Oct. 3, 2011

(87) PCT Pub. No.: WO2010/114622
PCT Pub. Date: Oct. 7, 2010

(65) Prior Publication Data
US 2012/0039960 A1 Feb. 16, 2012

Related U.S. Application Data

(60) Provisional application No. 61/166,680, filed on Apr. 3, 2009.

(51) Int. Cl.
*A61K 9/70* (2006.01)
(52) U.S. Cl.
USPC ............... 424/400; 424/49; 424/28; 424/45; 514/627; 514/305
(58) Field of Classification Search
USPC ......... 424/49, 400, 28, 45; 514/537, 627, 305
See application file for complete search history.

(56) References Cited

U.S. PATENT DOCUMENTS

| | | | |
|---|---|---|---|
| 3,832,460 A | 8/1974 | Kostic | |
| 5,209,724 A | 5/1993 | Dhaliwal | |
| 5,585,398 A | 12/1996 | Ernst | |
| 5,854,269 A | 12/1998 | Haslwanter | |
| 6,075,059 A | 6/2000 | Reader | |
| 6,413,499 B1 * | 7/2002 | Clay | 424/49 |
| 2004/0131665 A1 * | 7/2004 | Wepfer | 424/449 |
| 2007/0269465 A9 * | 11/2007 | Fita | 424/400 |

FOREIGN PATENT DOCUMENTS

JP 2004196786 7/2004

OTHER PUBLICATIONS

Sigma: Product Information of Hyaluronidase; Oct. 2002.*
Blanton, et al., "Avoiding complications in local anesthesia induction Anatomical considerations," Journal of the American Dental Association, 134:888-893 (2003).
Carroll et al., "The role of adrenergic receptors and pain: The good, the bad, and the unknown," Seminars in Anesthesia, Perioperative Medicine and Pain, 26:17-21 (2007).
Columb et al., "Local anaesthetic agents," Anaesthesia And Intensive Care Medicine, 128-132 (2004).
Corbo et al., "Drug absorption through mucosal membranes: effect of mucosal route and penetrant hydrophilicity," Pharmaceutical Research, 6(10):848-852 (1989).
Croda, "Minimizing Irritation Potential, Super Refined Oleic Acid," phamplet 2 pages (2011).
Dean, "Formulation: Nasal Drug Delivery," Pharmaceutical Formulation and Quality, 3 pages (2005).
Djupesland, "Breath-Actuated Bi-Directional Delivery sets the Nasal Market on a New Course," OptiNose Drug Delivery Devices, www.ondrugdelivery.com, pp. 20-23 (2005).
Eccles et al., "Menthol: Effects on Nasal Sensation of Airflow and the Drive to Breathe," Current Allergy and Asthma Reports, 3:210-214 (2003).
Franz et al., "Liposome-encapsulated ropivacaine for intraoral topical anesthesia," OOOE, 110(6):800-804 (2010).
Franz-Montan et al., "Liposome-Encapsulated Ropivacaine For Topical Anesthesia of Human Oral Mucosa," Anesthesia and Analgesia, 104(6):1528-1531 (2007).
Gabriel et al., "Alpha 2 agonists in regional anesthesia and analgesia," Current Opinion in Anaesthesiology, 14:751-753 (2001).
Gertler et al., "Dexmedetomidine: A novel sedative-analgesic agent," BUMC Proceedings, 14(1):13-21 (2001).
Grant "The Holy Grail: Long-acting local anaesthetics and liposomes," Best Practice & Research Clinical Anaesthesiology, 16(2):345-352 (2002).
Guay, "Methemoglobinemia related to local anesthetics: a summary of 242 episodes," Anesthesia and Analgesia, 108(3):837-845 (2009).
Haase et al., "Comparing anesthetic efficacy of articaine versus lidocaine as a supplemental buccal infiltration of the mandibular first molar after an inferior alveolar nerve block," Journal of the American Dental Association, 139(9):1228-1235 (2008).
Hall et al., "Oral Clonidine Pretreatment Prior to Venous Cannulation," Anesthesia Progress, 53:34-42 (2006).
Hersh et al., "The pharmacokinetics and cardiovascular effects of high-dose articaine with 1:100,000 and 1:200,000 epinepherine," Journal of the American Dental Association, 137:15672-1571 (2006).
Ishikawa et al., "Insoluble Powder Formulation as an Effective Nasal Drug Delivery System," Pharmaceutical Research, 19(8):1097-1104 (2002).
Jadhav et al., "Nasal Drug Delivery System—Factors Affecting and Applications," Current Drug Therapy, 2:27-38 (2007).

(Continued)

Primary Examiner — Fereydoun G Sajjadi
Assistant Examiner — Yanzhi Zhang
(74) Attorney, Agent, or Firm — Ropes & Gray LLP; Karen Mangasarian; Raymond M. Doss

(57) ABSTRACT

The present invention relates to tetracaine based anesthetic formulations and methods of use thereof. The invention further relates to topical formulations of tetracaine and methods of topically anesthetizing body tissues. The present invention also relates to tetracaine based dental anesthetic formulations and methods for anesthetizing the maxillary dental arch using these formulations.

45 Claims, 3 Drawing Sheets

(56) References Cited

OTHER PUBLICATIONS

Johnson et al., "Trigeminal Pathways Deliver a Low Molecular Weight Drug from the Nose to the Brain and Orofacial Structures," Molecular Pharmaceutics, 9(30):884-893 (2010).
Kamaya et al, "Combined effects of dissociable and undissociable local anesthetics upon ATP-induced firefly bioluminescence.," PNAS, 73(6):1868-1871 (1976).
Kaufman et al., "A Survey of Pain, Pressure, and Discomfort Induced by Commonly Used Oral Local Anesthesia Injections," Anesthesia Progress, 52:122-127 (2005).
Kimbell et al., "Characterization of Deposition from Nasal Spray Devices Using a Computational Fluid Dynamics Model of the Human Nasal Passages," Journal of Aerosol Medicine, 20(1):59-74 (2007).
Kravitz, "The use of compound topical anesthetics," Journal of the American Dental Association, 138(10):1333-1339 (2007).
Kruskal et al., "Use of Ranks in One-Criterion Variance Analysis," Journal of the American Statistical Association, 47(260):583-621 (1952).
Lipkind et al., "Molecular modeling of local anesthetic drug binding by voltage-gated sodium channels," Molecular Pharmacology, 68(6):1611-1622 (2005).
Liu et al., "Menthol facilitates the skin analgesic effect of tetracaine gel," International Journal of Pharmaceutics, 305(1-2):31-36 (2005).
Local Anesthetics, Chapter 15: Local Anesthetic Agents, , http://www.pharmacology2000.com/Central/Local_Anes/LAobj1.htm, 6 pages; printed Nov. 4, 2011.
Local Anesthetics, NYSORA—The New York School of Regional Anesthesia, http://www.nysora.com/regional_anesthesia/equipment/3116-local_anesthetics.html?print, 23 pages; printed Nov. 4, 2011.
MacPherson et al., "More than cool: Promiscuous relationships of menthol and other sensory compounds," Molecular and Cellular Neuroscience, 32(4):335-343 (2006).
Martin et al., "Effects of benzyl alcohol on PTH receptor-adenylate cyclase system of canine kidney," American Journal of Physiology, 248(1 pt 1):E31-E35 (1985).
Maze et al., "$\alpha_2$ Adrenoceptors in Pain Modulation : Which Subtype Should Be Targeted to Produce Analgesia?," Anesthesiology, 92:934-936 (2000).
Mishunin, "A method for potentiation of local anesthesia for tooth removal and pulp extirpation," Stomatologlia (Mosk), 81(4):42-43 (2002).
Noorily et al., "Cocaine, lidocaine, tetracaine: which is best for topical nasal anesthesia?," Anesthesia and Analgesia, 81:724-727 (1995).
Oka et al., "The addition of epinephrine to tetracaine injected intrathecally sustains an increase in glutamate concentrations in the cerebrospinal fluid and worsens neuronal injury," Anesthesia & Analgesia, 93(4):1050-1057 (2001).
Omote et al., "Effects of Verapamil on Spinal Anesthesia with Local Anesthetics," Anesthesia and Analgesia, 80:444-448 (1995).
Ostrow, "Nasal Spray May Take Place of Needle," Copyright WIVB.com, published Feb. 26, 2009 (downloaded May 15, 2012).
Oxymetazoline Hydrochloride in Combination With Nasal Glucocorticosteroid for Perennial Allergic and Non-allergic Rhinitis in Subjects With Persistent Nasal Congestion, http://clinicaltrials.gov/ct2/show/NCT00584662, ClinicalTrials.gov, 4 pages; printed Nov. 4, 2011.
Raposio et al., "Comparative effectiveness of benzyl alcohol 0.9% as a local anaesthetic for minor plastic surgery procedures," European Journal of Plastic Surgery, 22:125-127 (1999).
Rathbone et al., "The oral cavity as a site for systemic drug delivery," Advanced Drug Delivery Reviews, 13:1-22 (1994).
Reader et al., "Local Anesthesia for endodontic pain," Endodontic Topics, 3:14-30 (2002).
Reyes et al., "Effect of the anesthetics benzyl alcohol and chloroform on bilayers made from monolayers," Biophysical Journal, 28(2):259-279 (1979).
Rovner, "Cooling Compounds Conquer Chronic Pain. Interaction with nerves reveals mechanism to block long-term pain," Chemical & Engineering News, http://pubs.acs.org/cen/news/84/i36/8436cooling.html, 2 pages (2006).
Sabetkasaie et al., "Clonidine and guanfacine-induced antinociception in visceral pain: possible role of alpha$_2$/I$_2$ binding sites," European Journal of Pharmacology, 501:95-101 (2004).
Sarkar, "Drug Metabolism in he Nasal Mucosa," Pharmaceutical Research, 9(1):1-9 (1992).
Sawynok, "Topical and Peripherally Acting Analgesics," Pharmacological Reviews, 55(1):1-20 (2003).
Schneck, "Local anesthesia in otolaryngology. A re-evaluation," Annals of Otology, Rhinology and Laryngology, 81:65-72 (1975).
Taylor et al., "Modification of Local Anesthetic Toxicity by Vasoconstrictors," Anesthesia Progress, 36:79-87 (1989).
Turker et al., "Nasal route and drug delivery systems," Pharmacy World and Science, 26(3):137-142 (2004).
Tyden et al., "Metabolic activation of 2,6-xylidine in the nasal olfactory mucosa and the mucosa of the upper alimentary and respiratory tracts in rats," Toxicological Sciences, 81(2):263-272 (2004).
Wahl et al., "New medical management techniques for acute exacerbations of chronic rhinosinusitis," Current Opinion in Otolaryngology & Head and Neck Surgery, 11:27-32 (2003).
Wermeling et al., "Analgesic effects of intranasal butorphanol tartrate administered via a unit-dose device in the dental impaction pain model: a randomized, double-blind, placebo-controlled, parallel-group study," Clinical Therapeutics, 27(4):430-440 (2005).
Arora et al., "Permeability issues in nasal drug delivery," Drug Discovery Today, 7(18):967-975 (2002).
Becker et al., "Essentials of local anesthetic pharmacology," Anesthesia Progress, 53(3):98-108 (2006 (quiz 109-10).
Bernard et al., "Dose-Range Effects of Clonidine Added to Lidocaine for Brachial Plexus Block," Anesthesiology, 87(2):277-284 (1997).
Raposio et al., "Comparative effectiveness of benzyl alcohol 0.9% as a local anaesthetic for minor plastic surgery procedures," European Journal of Plastic Surgery, 22:125-127 (1999).
"Deposition Comparison, A Scintigraphic Study," A New Spin on Nasal Drug Delivery, 6 pages, http://www.kurvetech.com/TechnologClinical.asp, (2005).
106th Congress. Needlestick Safety and Prevention Act. Public Law 106-430. Nov. 6, 2000.
Cleveland et al., "Preventing percutaneous injuries among dental health care personnel," Journal of the American Dental Association, 138(20):169-178 (2007).
Clontz, "Microbial Limit and Bioburden Tests Validation Approaches and Global Requirements," 2nd Edition, pp. 44-47 (2008).
Covino et al., Pharmacology of local anesthetic agents, Journal of Dental Research, 60(8):1454-1459 (1981).
Dionne et al., "Assessing the need for anesthesia and sedation in the general population," Journal of the American Dental Association, 129(2):167-173 (1998).
Du, "Local Anesthetics," 5 pages, http://www.uic.edu/classes/pcol/pcol331/dentalhandouts2005/dentlecture33.pdf (2005).
Gatt, "Ropivacaine in Obstetric Anaesthesia," General Properties of Ropivacaine, http://www.manbit.com/oa/C4.htm (2003).
Göthert et al., Preface. Annals of the New York Academy of Sciences, 881: xiii-xv. doi: 10.1111/j.1749-6632.1999.tb09334.x (1999).
Heft et al., "An experimental basis for revising the graphic rating scale for pain," Pain, 19(2):153-61 (1984).
Jain, "Pain Therapeutics, Drugs, Markets & Companies—Dental Pain," Jain PharmaBiotech, Basel, Switzerland, p. 133 (2007).
Johns et al., "Otolaryngology—head and neck surgery," Journal of the American Medical Association, 271(21):1698-1700 (1994).
Kaufman et al., "Difficulties in achieving local anesthesia," Journal of the American Dental Association, 108(2):205-208 (1984).
Kitagawa et al., "Possible mechanism of irreversible nerve injury caused by local anesthetics: detergent properties of local anesthetics and membrane disruption," Anesthesiology, 100(4):962-967 (2004).
Malamed, "Pharmacology of Local Anesthetics," Handbook of Local Anesthesia, Fourth Edition, Chapter 2, Part 1, pp. 24-36 (1997).
Malamed, "Active Forms of Local Anesthetics," Handbook of Local Anesthesia, Fourth Edition, Chapter 1, Part 1, pp. 14-18 (1997).

(56) References Cited

OTHER PUBLICATIONS

Malamed, "Clinical Action of Specific Agents," Handbook of Local Anesthesia, Fourth Edition, Chapter 4, Part 1, pp. 49-73 (1997).

Milgrom et al., "The prevalence and practice management consequences of dental fear in a major US city," Journal of the American Dental Association, 116(6):641-647 (1988).

Miller, "Local Anesthesia," Basic and Clinical Pharmacology, (Katzung, B. G., ed) Appleton-Lange, pp. 425-433 (1998).

Nasal Drug Delivery Blog, Intranasal Drug Delivery Market in United States to Reach US$ 2.6 Billion by 2010, According to New Report by Global Industry Analysts, Inc., (3 pages) (2007).

Schaller, "Transdermal Orthopedic USP Cream for Arthritis Joint Pain," http://www.personalconsult.com/articles/transdermalorthopedicuspcream.html, 8 pages (printed Mar. 28, 2013).

Shapiro, et al., "An analysis of variance test for normality (complete samples)," Biometrika, 52(3-4):591-611 (1965).

Stoelting, "Local Anesthetics," Pharmacology and Physiology in Anesthetic Practice, 3rd Edition, Chapter 7, pp. 158-181 (1999).

Tan et al., "Efficacy of intrathecal neostigmine for the relief of postinguinal hemiorrhaphy pain" Acta Anaesthesiologica Scandinavica, 44(9):1056-1060 (2000).

Tetzlaff, Department of General Anesthesiology, "Amino Ester Local Anesthetics," Cleveland Clinic Foundation: Department of General Anesthesiology, http://faculty.weber.edu/ewalker/Medicinal_Chemistry/topics/Psycho/local_a_ester.htm, 3 pages, printed Mar. 28, 2013.

Tucker et al., "Comparative Pharmacology of Local Anesthetics," Clinical Pharmacokenetics, 4(4):241-278 (1979).

Williams, "Local Anesthetics and Analgesia," Dept. of Otolaryngology, UTMB, Grand Rounds, http://www.utmb.edu/oto/Grand_Rounds_Earlier.dir/Local_Anes_1990.txt (9 pages) (1990).

Yoon et al., "Local anesthetics inhibit kinesin motility and microtentacle protrusions in human epithelial and breast tumor cells," Breast Cancer Research Treatment, 129(3):691-701 (2011).

Zhang et al., "Effect of oxymetazoline on healthy human nasal ciliary beat frequency measured with high-speed digital microscopy and mucociliary transport time," Annals of Otology, Rhinology and Laryngology, 117(2):127-33 (2008).

* cited by examiner

Cross-sectional Side View of the Human Nasal Cavity, Maxillary Dentition and Associated Nerves (Clay et al.; USP 6,413,499)

Spray Angle for Sprays 2 and 3

DENTAL ANESTHETIC COMPRISING TETRACAINE AND A VASOCONSTRICTOR FOR INTRANASAL ADMINISTRATION

This application is a United States National Stage Application under 35 U.S.C. §371 of International Application PCT/US2010/001002, filed Apr. 2, 2010, which claims priority to and the benefit of U.S. Provisional Application 61/166,680, filed Apr. 3, 2009, now expired. The entire disclosures of each of the above applications is hereby incorporated by reference.

TECHNICAL FIELD OF INVENTION

The present invention relates to tetracaine based anesthetic formulations and methods of use thereof. The invention further relates to topical formulations of tetracaine and methods of topically anesthetizing body tissues. The present invention also relates to tetracaine based dental anesthetic formulations and methods for anesthetizing the maxillary dental arch using these formulations.

BACKGROUND OF THE INVENTION

The most common means for anesthetizing maxillary teeth is the use of an infiltration injection. For example, the patient may receive a needle penetration and injection of a local anesthetic solution at the approximate apex of the root on the buccal surface of a tooth (or teeth) to be treated. A maxillary palatal injection of dental local anesthetic can be used for regional block anesthesia of teeth. The patient may also receive a maxillary palatal injection of local anesthesia in order to effect regional nerve blocks.

Dental anxiety, including needle or shot discomfort and phobia, is a long-standing barrier to regular dental care. In a survey conducted by the American Dental Association, 27% of the people surveyed indicated "fear of pain" as a reason to avoid dental visits. Needle injection of local anesthetic is recognized as the most anxiety-provoking procedure in dentistry for children and adults. Not only can the injection of local anesthetics produce fear, pain and an increase in blood pressure, but the of local anesthetics produce fear, pain and an increase in blood pressure, but the increased stress of injection can result in fainting, hyperventilation, convulsions, shock, hypertension, cardiac arrest, respiratory collapse, acute allergic reaction to preservatives, bronchospasm, angina, and organ system toxicity in medically compromised patients. Further, local injections into target nerves can sometimes lead to permanent numbness as a result of needles damaging and/or cutting nerves. In rare cases, a severe overdose of injectable anesthetic or accidental, rapid intravascular injection of the anesthetic can even lead to death. The act of injecting is invasive (conceptually, psychologically, and physically) and is a major reason worldwide why people avoid regular dental care and see their dentists only in an emergency. In fact, some studies indicate that millions of people in the US are afraid of dental treatments because of pain. Without regular dental care, tooth caries, gum disease and oral cancer may be left undetected and can result in infection and serious, systemic health issues.

In addition, the risk of exposure to bloodborne pathogens via needlesticks is a recognized occupational hazard in dentistry. Since 1991, the Occupational Safety and Health Administration ("OSHA") has enforced a Bloodborne Pathogens Standard that requires employers to identify, evaluate and implement safer medical devices to eliminate or minimize employee exposure to bloodborne pathogens. The standard was revised in 2001 when Congress passed the Needlestick Safety and Prevention Act. The Act set forth in greater detail employers' obligations under the Bloodborne Pathogens standard and specifically indicated that a "safer medical device" includes needleless systems. Thus, further incentive exists to develop anesthetics that can be delivered without the use of needles and comply with U.S. federally mandated engineered work practice controls.

Lidocaine, the most widely used local dental anesthetic today, was first introduced in the 1940s. Despite many attempts at developing needle-free anesthetic, the only widely-used non-injectable, subsurface local anesthetic commercially available today is Oraqix® gel. While Oraqix® can be used in periodontal pockets during scaling or root-planing procedures, it does not provide adequate anesthesia for use in procedures such as filling, crowns and root canals. Further, while many advances in the comfort of dentistry have been made, such as behavior modification therapy, topical numbing around the injection site, nitrous oxide, hypnosis, and TENS units, none of these advances has eliminated the need for needle injection.

Nasal administration of anesthetics has also been disclosed, for example, in U.S. Pat. No. 6,413,499.

Thus, there remains a need for alternative and effective anesthetics. In particular, there remains a need for alternative and effective anesthetics and means for administering such anesthetics to a patient in order to anesthetize the patient's teeth without creating extra oral soft tissue numbness, discomfort, or phobia in the patient.

SUMMARY OF THE INVENTION

The present invention provides a tetracaine based anesthetic and methods of use thereof.

In one aspect, the present invention provides a tetracaine based anesthetic formulation which is useful for anesthetizing at least a portion of a body part, organ, or tissue.

In some embodiments, the present invention provides a nasal tetracaine based dental anesthetic formulation which is useful for anesthetizing the maxillary dental arch. The invention is based on delivering anesthetic to specific areas in the nasal cavity and/or nasal sinuses such as the maxillary sinus. The invention is also based on delivering the anesthetic to the anterior dental plexus, extensions of the middle superior nerve, the posterior superior alveolar nerve, the nociceptors of the facial and buccal nerve, and/or the sphenopalatine (pterygopalatine) ganglion.

The nerves of the upper teeth are like branches of a tree that extend through the nasal cavity down into the teeth. The pharmaceutical composition of the present invention is administered into the rear of the nasal cavity, affecting the base, or "trunk," of the nerve pathways. This anesthetizes the branches that transmit nerve impulses from all of the upper teeth (other than the two wisdom teeth and the second molar on each side) as well as the A delta and C pain fibers of the facial soft tissue. In some cases, the second molars are indeed anesthetized.

In one aspect, the invention provides a pharmaceutical composition comprising a) tetracaine, or a pharmaceutically acceptable salt thereof; b) a vasoconstrictor; and c) a pharmaceutically acceptable carrier. In other embodiments, the pharmaceutical composition comprises a) tetracaine, or a pharmaceutically acceptable salt thereof; b) a vasoconstrictor; c) a preservative; d) a viscosity enhancing agent; and e) a pharmaceutically acceptable carrier. In some embodiments, the composition comprises about 2.0-5.0% (w/v) tetracaine. In some embodiments, the composition comprises about 2.25-

4.75% (w/v) tetracaine. In other embodiments, the composition comprises about 2.5-4.0% (w/v) tetracaine. In yet other embodiments, the composition comprises about 2.5-3.5% (w/v) tetracaine. In other embodiments, the composition comprises about 3% (w/v) tetracaine. In some embodiments, the pharmaceutical composition is for intranasal administration.

The vasoconstrictors that may be included in the pharmaceutical compositions of the invention (including the intranasal pharmaceutical composition) include, but are not limited to, indirect $\alpha_1$-adrenergic; calcium channel blockers; meperidine; imidazole drugs such as oxymetazoline and xylometazoline; $\alpha_2$-adrenergic agonists such as guanfacine; imidazoline ($I_1$) ligands; direct $\alpha_2$-adrenergic agonists such as clonidine; substance P blockers/reducers such as capsaicin; I-menthol; icilin; epinephrine (i.e., adrenaline); levonordefrin (i.e., nordefrin); and glutamate receptor inhibitors; or pharmaceutically acceptable salts thereof. In some embodiments, the vasoconstrictor is oxymetazoline, or a pharmaceutically acceptable salt thereof. In other embodiments, the oxymetazoline is an oxymetazoline HCl salt.

In some embodiments, the pharmaceutical composition comprises about 0.01-1.0% (w/v) oxymetazoline HCl. In other embodiments, the pharmaceutical composition comprises about 0.05% (w/v) oxymetazoline.

In some embodiments, the pharmaceutical composition (including the intranasal pharmaceutical composition) further comprises a preservative. In some embodiments, the preservative includes, but is not limited to, sugar alcohols (e.g., sorbitol and mannitol), ethanol, benzyl alcohol, isopropanol, cresol, chlorocresol, and phenol. In some embodiments, the preservative is benzyl alcohol. In some embodiments, the intranasal pharmaceutical composition comprises about 0.5-2.0% (w/v) benzyl alcohol. In other embodiments, the pharmaceutical composition comprises about 0.9% (w/v) benzyl alcohol.

In some embodiments, the pharmaceutical composition (including the intranasal pharmaceutical composition) further comprises a viscosity enhancing agent. In some embodiments, the viscosity enhancing agent includes, but is not limited to methylcellulose, hydroxyethylcellulose, hydroxypropylmethylcellulose and smart hydrogel. In some embodiments, the viscosity enhancing agent is hydroxyethylcellulose. In some embodiments, the intranasal pharmaceutical composition comprises about 0.01-1.0% (w/v) hydroxyethylcellulose. In other embodiments, the intranasal pharmaceutical composition comprises about 0.05% (w/v) hydroxyethylcellulose.

In some embodiments, the pharmaceutical composition is formulated as a gel or a liquid. In some embodiments the liquid is water, a sugar alcohol, an alcohol (e.g., ethanol), or any other anesthetic solvent that is biologically compatible with the target tissue.

In some embodiments, the pH of the pharmaceutical composition is between about 4.0 to about 7.5. In other embodiments, the pH of the pharmaceutical composition is between about 4.0 to about 6.5. In another embodiment the pharmaceutical composition has a pH of about 5.5 to about 6.5. In further embodiments, the pharmaceutical composition has a pH of about 6.0 to about 6.5.

In a particular embodiment, the pharmaceutical composition comprises tetracaine, oxymetazoline and benzyl alcohol. In another embodiment, the pharmaceutical composition comprises tetracaine HCl, oxymetazoline HCl, anhydrous citric acid (for pH control), sodium hydroxide (for pH adjustment), benzyl alcohol, hydrochloric acid (for pH control), hydroxyethylcellulose, and purified water. In a more particular embodiment, the pharmaceutical composition of the present invention comprises the components, and respective amounts, listed in Table 1 below (referred to herein as the "Table 1 formulation"). In a further embodiment, the Table 1 formulation is for intranasal administration.

TABLE 1

| Ingredient | Formulation (% w/v) |
| --- | --- |
| Tetracaine hydrochloride, USP | 3.00 |
| Oxymetazoline hydrochloride, USP | 0.05 |
| Citric acid anhydrous, USP | 1.00 |
| Sodium hydroxide, NF | q.s. |
| Benzyl alcohol, NF | 0.90 |
| Hydrochloric acid, NF | q.s. |
| Hydroxyethylcellulose, NF (5000 cps) | 0.05 |
| Purified water, USP | q.s. to 100% |

In another aspect, the present invention provides a method of anesthetizing at least a portion of a body part, organ, or tissue by administering a pharmaceutical composition of the invention. In some embodiments, such a pharmaceutical composition is administered topically. In some embodiments, the tissue is epithelial tissue. In other embodiments, the tissue is mucosal tissue. In yet other embodiments, the mucosal tissue is a tissue or membrane present in the ear, throat, mouth (e.g., gums), eye, nose, rectal area and/or the urogenital tract (such as the vagina).

In another aspect, the invention provides a method for anesthetizing at least a portion of a patient's maxillary dental arch (and pain fibers external to the dental arch) in a subject comprising selectively delivering into the nasal cavity of the subject a pharmaceutical composition of the invention, wherein at least a portion of the pharmaceutical composition is absorbed by nasal tissue located at the rear of the nasal cavity in the vicinity of the sphenopalatine ganglion and, consequently, the maxillary nerve (and/or structures that communicate with the maxillary nerve), thereby anesthetizing at least a portion of the maxillary dental arch (and pain fibers outside, but around the maxillary arch) of the subject of the subject. In some embodiments, the pharmaceutical compositions is delivered into the nasal sinus and/or rear of the nasal cavity of the subject. In some embodiments, the tissues around the maxilla are also anesthetized. In some embodiments, the pharmaceutical composition is delivered by nebulization, ionophoresis, laser, ultrasound (typically at greater than 20,000 cycles/second) or spraying. In some embodiments the pharmaceutical composition and/or target tissue are chilled or heated before administration. In some embodiments, the pharmaceutical composition is delivered by spraying. In other embodiments, the delivered spray is a stream or a plume.

In some embodiments, the method comprises spraying the intranasal pharmaceutical composition of the invention 1-5 times into each of the nostrils of the subject. In other embodiments, the method comprises spraying the pharmaceutical composition of the invention 3 times into each of the nostrils of the subject. In some embodiments, each of the sprays are administered within about 1-10 minutes, of each other. For example, spray #1 may be administered, followed by an interval of about 1-10 minutes, after which spray #2 is administered, followed by an interval of about 1-10 minutes after which spray #3 is administered, etc. In some embodiments, the interval between sprays is about 1-6 minutes. In some embodiments, the interval between sprays is about 2-6 minutes. In other embodiments, the interval between sprays is about 3-5 minutes. In yet other embodiments, the interval between sprays is about 4 minutes.

In some embodiments, the method comprises delivering a known (e.g., metered) amount of tetracaine into the nasal cavity of the subject. In some embodiments, the method comprises delivering about 12-50 mg of tetracaine into the nasal sinuses and/or rear of the nasal cavity of the subject. In other embodiments, the method comprises delivering about 15-24 mg of tetracaine into the nasal sinuses and/or rear of the nasal cavity of the subject. In another embodiment, the method comprises delivering about 15-20 mg of tetracaine into the nasal sinuses and/or rear of the nasal cavity of the subject.

In some embodiments, the particle size of the pharmaceutical composition delivered to the rear of the nasal sinuses and/or rear of the nasal cavity is about 5-50 microns (μm). In other embodiments, the particle size of the pharmaceutical composition is about 10-20 microns. In other embodiments, the pharmaceutical composition is delivered in a manner such that at least 85% of the particles are at least about 10 microns or larger. In yet other embodiments, the particle size of the pharmaceutical composition is about 10 microns or larger.

In another aspect, the invention provides a spray device for intranasal delivery of a pharmaceutical composition of the present invention. In some embodiments, the spray device is capable of delivering the intranasal pharmaceutical composition to the nasal tissue located at the rear of the nasal cavity. In other embodiments, the spray device is capable of delivering the intranasal pharmaceutical composition to the nasal tissue located in the nasal sinuses and at the rear of the nasal cavity, in the vicinity of the maxillary nerve and/or structures that communicate with the maxillary nerve. In yet other embodiments, the spray device is pre-filled with an intranasal pharmaceutical composition of the present invention.

DETAILED DESCRIPTION OF THE INVENTION

Figure 1:
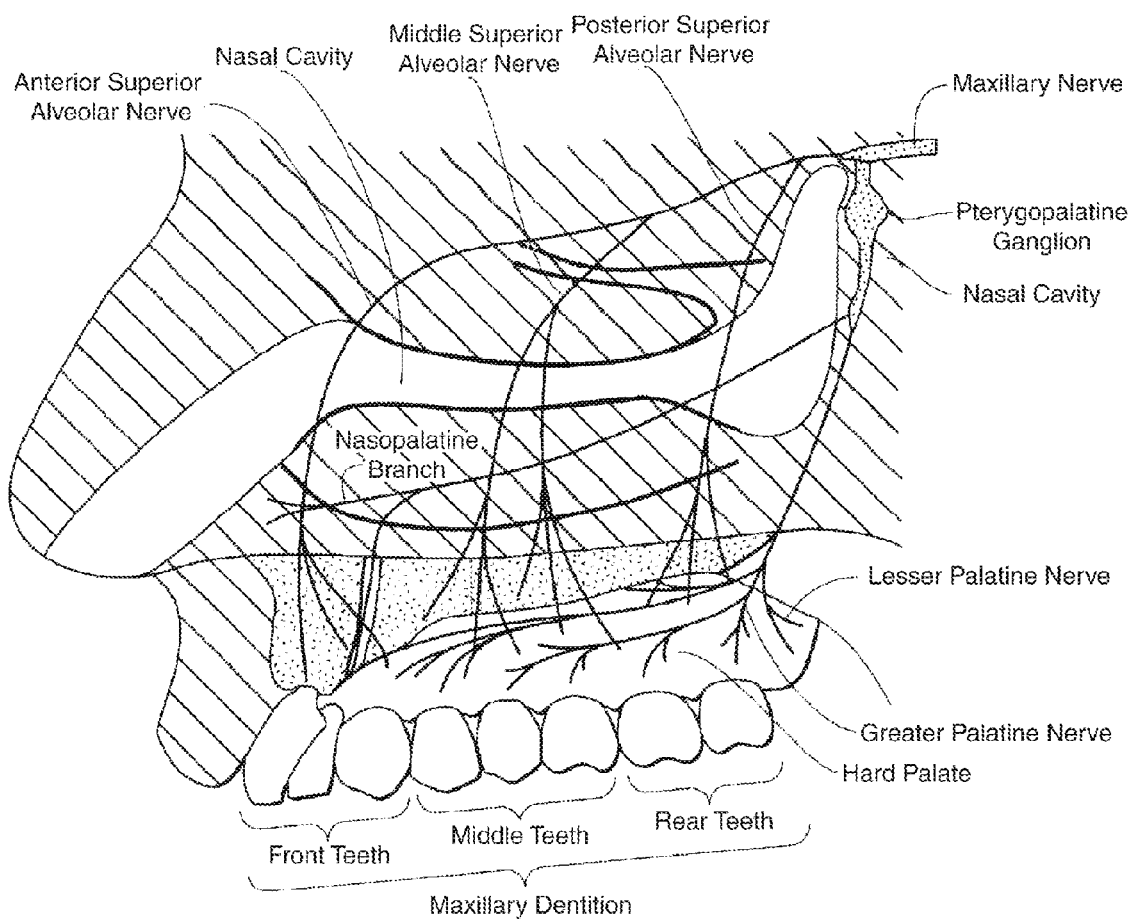
FIG. 1 is a cross-sectional side view of a person's nasal cavity, maxillary dentition and associated nerves. Both the greater and lesser palatine nerves originate at the pterygopalatine (sphenopalatine) ganglion. The anterior, middle and posterior superior alveolar nerves originate at the maxillary nerve. The nasopalatine branch of the anterior superior alveolar nerve communicates between the alveolar nerves and the palatine nerves. The nerve endings of the anterior superior alveolar nerve are located in the front teeth. The nerve endings of the middle superior alveolar nerve are located in the middle teeth (i.e., the first molars and upper first and second bicuspids on both sides of the maxillary arch). The nerve endings of the posterior superior alveolar nerve are located in the rear teeth (i.e., the distal one half of the upper first molars and second and third molars). These nerves and the preceding nerves (which are joined at the maxillary nerve) are primarily responsible for the transmission of pain impulses from the teeth to the brain. The greater palatine nerve, whose nerve endings are in the hard, is responsible (along with the preceding nerves) for the transmission of pain impulses from the hard palate to the brain. Similarly, the lesser palatine nerve, whose nerve endings are in the soft palate, is responsible (along with the preceding nerves) for the transmission of pain impulses from the soft palate to the brain.
Figure 2:
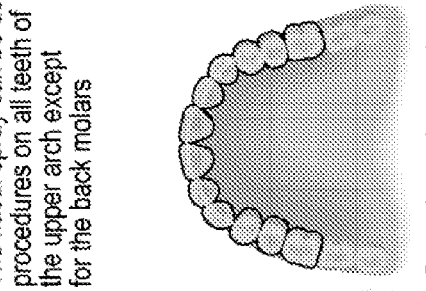
FIG. 2 compares methods of delivering local anesthetics by needle injection with a method of delivering an intranasal pharmaceutical composition of the present invention.
Figure 2:
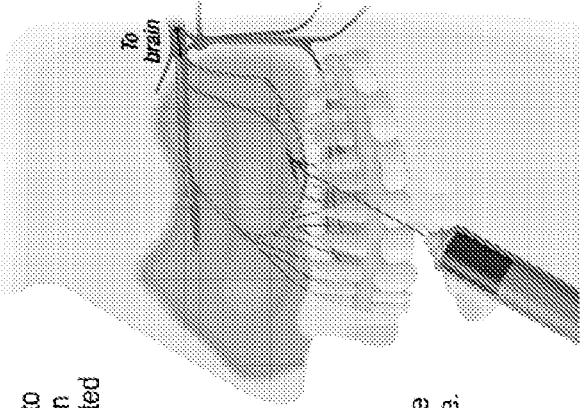
Figure 3:
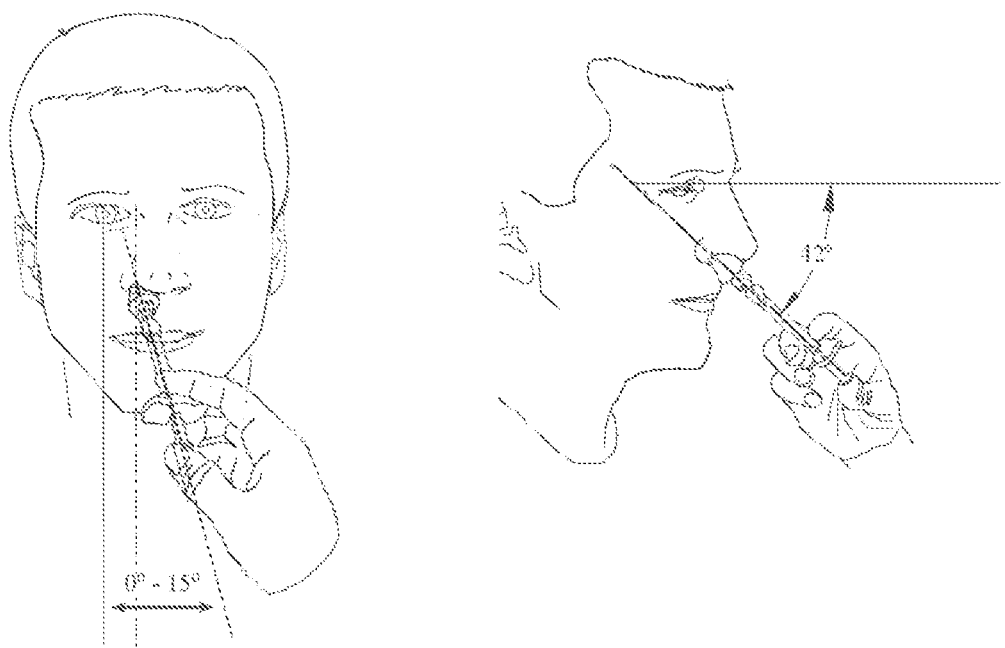
FIG. 3 illustrates the spray angles of the tip of the spray device (with respect to the horizontal plane) during administration of a nasal formulation.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

In order to further define the invention, the following terms and definitions are provided herein.

DEFINITIONS

"Anesthetizing" as used herein refers to administering an anesthetic compound (e.g., tetracaine) for the purpose of preventing sensation and/or reducing pain.

"Intranasal formulation" as used herein refers to a formulation that is delivered to the nasal cavity and/or nasal sinuses.

"Local anesthetic" as used herein refers to an anesthetic delivered near the nerve ending to be anesthetized which diffuses after introduction inside the tissue. A local anesthetic is capable of penetrating the tissue deep enough so as to reach the target nerves and nerve branches. A local anesthetic is different from a "topical anesthetic" in that a topical anesthetic only provides surface anesthesia to a depth of approximately 1-2 mm. A topical anesthetic does not penetrate deep enough in the tissue to reach nerve branches or teeth.

"Maxilla" as used herein refers to either of a pair of bones of the human skull fused to form the upper jaw. The maxilla is sometimes simply referred to as the upper jaw.

"Maxillary dental arch" or "maxillary arch" as used herein refers to the curved structure formed by the maxillary (upper) teeth in their natural position.

"Mucosal tissue" or "mucous tissue" as used herein refers to a type of epithelial tissue. Mucosal tissue refers to the layer of tissue which covers the surface of organs or lines a cavity. Non-limiting examples of mucosal tissue include, tissue in the ear, throat, mouth, eye, nose, rectal area and/or the urogenital tract (such as the vagina).

"Pulpal anesthesia" as used herein refers to a level of anesthesia such that when a electric pulp testing (EPT) stimulation (i.e., a reading of 65 on the pulp tester) is administered to a tooth, the subject indicates no pain sensation in the tooth.

"Preceding nerves" as used herein refers to nerve endings and nerves located upstream, usually present in a more central neural bundle, from a particular reference nerve.

"Subject" as used herein refers to an animal including a mammal (e.g., a human).

"Tetracaine" (sometimes referred to as "amethocaine") as used herein refers to (2-(dimethylamino)ethyl 4-(butylamino)benzoate) and any salt thereof. Tetracaine HCl refers to the HCl salt of 2-(dimethylamino)ethyl 4-(butylamino) benzoate.

Pharmaceutical Compositions

The present invention provides tetracaine based anesthetic formulations. These formulations are useful for anesthetizing at least a portion of a body part, organ, or tissue. In one aspect, the present invention provides a pharmaceutical composition for anesthetizing at least a portion of a body part, organ, or tissue by administering a pharmaceutical composition of the invention. In some embodiments, the pharmaceutical composition described herein is delivered directly to the target body part, organ, or tissue.

In some embodiments, the target tissue is epithelial tissue. In other embodiments, the target tissue is mucosal tissue. In yet other embodiments, the mucosal tissue is a tissue or membrane present in the ear, throat, mouth (e.g., gums), eye, nose, rectal area and/or the urogenital tract (such as the vagina).

In some embodiments, the present invention provides intranasal formulations of tetracaine. Such formulations are useful for anesthetizing the maxillary dental arch and pain fibers around the maxillary dental arch. Such formulations are useful as local anesthetics.

Tetracaine is unique in that it is both stable and highly protein bound compared to nearly all other local anesthetics. Because of its protein-bound nature and smaller molecular weight, tetracaine is better able to penetrate and adhere to the protein-covered membranes of nerve cells and is better able to penetrate the nerve so as to induce an anesthetic effect (especially when present in a formulation containing at least some of, e.g., vasoconstrictors, surfactants, emulsifiers, solvents, pH modifiers and preservatives) when compared to other ester-based anesthetics such as cocaine, procaine, chloroprocaine and benzocaine. In addition, other ester-based local anesthetics are very toxic in small amounts and have also been shown to be unstable. Amide-based local anesthetics such as lidocaine, mepivacaine, bupivacaine, etidocaine, prilocaine, and ropivacaine, while protein bound, are not as effective as tetracaine (especially when tetracaine is part of one of the formulations of the present invention).

As such, the present invention provides a pharmaceutical composition suitable for administration of tetracaine or a pharmaceutically acceptable salt thereof. In certain embodiments, the pharmaceutical composition comprises a) tetracaine, or a pharmaceutically acceptable salt thereof; b) a vasoconstrictor; and c) a pharmaceutically acceptable carrier. In other embodiments, the pharmaceutical composition comprises a) tetracaine, or a pharmaceutically acceptable salt thereof; b) a vasoconstrictor; c) a preservative; d) a viscosity enhancing agent; and e) a pharmaceutically acceptable carrier. In some embodiments, the composition comprises about 2.0-5.0% (w/v) tetracaine. In some embodiments, the composition comprises about 2.25-4.75% (w/v) tetracaine. In other embodiments, the composition comprises about 2.5-4.0% (w/v) tetracaine. In yet other embodiments, the pharmaceutical composition comprises about 2.5-3.5% (w/v) tetracaine. In a particular embodiment, the pharmaceutical composition comprises about 3% (w/v) tetracaine. In some embodiments, the pharmaceutical composition is for intranasal administration.

Any vasoconstrictor may be used in the pharmaceutical composition of this invention. The vasoconstrictors used in the pharmaceutical compositions of the invention has several purposes. First, the vasoconstrictor shrinks the tissue (e.g., nasal tissue) thereby enhancing penetration of the anesthetic into the tissue (e.g., deeper into the nasal cavity). Second, once the vasoconstrictor has been absorbed into the desired area, it inhibits systemic migration of the anesthetic, thereby allowing the anesthetic to remain at a desired site. Third, the vasoconstrictor reduces blood flow to the desired tissue, thereby increasing the duration of the anesthetic's effectiveness (typically by activating G-protein coupled receptors which render metallic ionophores in the nerve membrane more sensitive to the tetracaine base). Typical vasoconstrictors useful in the pharmaceutical compositions of this invention include but are not limited to indirect $\alpha_1$-adrenergic agonists such as phenylephrine; calcium channel blockers; meperidine; imidazole drugs such as oxymetazoline and xylometazoline; $\alpha_2$-adrenergic agonists such as guanfacine; imidazoline ($I_1$) ligands; direct $\alpha_2$-adrenergic agonists such as clonidine; substance P blockers/reducers such as capsaicin; I-menthol; icilin; and glutamate receptor inhibitors; or pharmaceutically acceptable salts thereof. In some embodiments, the vasoconstrictor includes but is not limited to oxymetazoline, xylometazoline, guafacine, clonidine, phenylephrine, meperidine, capsaicin; I-menthol; icilin and pharmaceutically acceptable salts thereof In some embodiments, the vasoconstrictor is oxymetazoline, or a pharmaceutically acceptable salt thereof. In other embodiments, the oxymetazoline is an oxymetazoline HCl salt.

The concentration of vasoconstrictor used in the pharmaceutical composition of the instant invention will depend on the specific vasoconstrictor and the desired vasoconstricting effect. Typical ranges of concentrations include but are not limited to about 0.01-5% (w/v). In some embodiments, the composition comprises about 0.01-1.0% (w/v) (e.g., oxymetazoline HCl salt). In yet other embodiments, the composition comprises about 0.05% (w/v) (e.g., oxymetazoline HCl salt).

In addition to its vasoconstricting activity, oxymetazoline has been shown to have a degree of anesthetic affect. Oxymetazoline affects G-protein coupled receptors and, in turn, $K^+$, $Na^+$, and $Ca^{2+}$ channels present in nerve cells. In particular, oxymetazoline enhances $K^+$, $Na^+$, and $Ca^{2+}$ permeability such that the nerve is no longer polarized and, thus, is unable to fire and transmit pain impulses.

In some embodiments, the pharmaceutical composition of this invention further comprises a preservative. Examples of preservatives include, but are not limited to sugar alcohols (e.g., sorbitol and mannitol), ethanol, benzyl alcohol, isopropanol, cresol, chlorocresol, phenol and benzalkonium chloride (BAK). In some embodiments, the preservative is benzyl alcohol. Benzyl alcohol is particularly desirable because it exhibits an anesthetic effect and works to enhance the effect of tetracaine in a synergistic manner.

The concentration of preservative used in the pharmaceutical composition of the instant invention will depend on the specific preservative. Typical ranges of concentrations of preservatives are about 0.1-5% (w/v). In some embodiments, the composition comprises about 0.5-2.0% (w/v). In other embodiments, the composition comprises about 0.9% (w/v) (e.g., benzyl alcohol).

The anesthetic, vasoconstrictor and other agents used in the compositions of the present invention may be dispersed in an appropriate carrier in order to control the dosage, absorption rate and other desired properties. Pharmaceutically acceptable carriers useful in the present invention include but are not limited to aqueous carriers, gel carriers, emulsifiers, surfactants, time release vehicles, nanoparticles, microspheres, intra- and para-cellular transport chemicals, polymers, and chitin. Examples of aqueous carriers include, but are not limited to, water, buffers (e.g., phosphate buffer, citrate buffer), sugar alcohols, alcohols such as ethanol, or any other solvent that is biologically compatible with the target tissue.

Saline is not an appropriate carrier for use with the compositions of the present invention. Specifically, it has been discovered that the compositions of the present invention are unstable in saline as exhibited by the formation of a precipitate.

The pH of the pharmaceutical composition of the present invention is typically adjusted to be compatible with the pH of the tissue to which it is being administered (e.g., the nasal cavity). Typically, the composition has a pH of about 4.0-6.5. In some embodiments, the composition has a pH of about 5.5-6.5. In further embodiments, the pharmaceutical composition has a pH of about 6.0 to about 6.5. The skilled artisan will appreciate that higher or lower pHs than those recited may be required and would readily know how to adjust the pH accordingly.

In some embodiments, the pharmaceutical composition of this invention further comprises a viscosity enhancing agent. Examples of viscosity enhancing agents include, but are not limited to methylcellulose, hydroxyethylcellulose, hydroxypropylmethylcellulose and smart hydrogel. In some embodiments, the viscosity enhancing agent is hydroxyethylcellulose.

Viscosity enhancing agents aid in controlling the mobility of the formulation before, during, and after application of the formulation to a target body part, tissue or organ. For example, viscosity enhancing agents aid in controlling the amount of formulation that either drips out of the nostrils or into the throat of the subject by reducing the mobility of the applied formulation. Viscosity enhancing agents also increase the amount of time the formulation is in contact with the vasculature (e.g., nasal vasculature) which helps to increase the uptake efficiency of the formulation to the vasculature. In addition, viscosity enhancing agents further dilute moieties present in the nasal passage that degrade esters (e.g., esterase) and can be mildly cilio-inhibitory.

The concentration of viscosity enhancing agent used in the pharmaceutical composition of the instant invention will depend on the specific viscosity enhancing agent. Typical ranges of viscosity enhancing agents, include 0.01 to 5% (w/v). In some embodiments, the pharmaceutical composition comprises about 0.01-1.0% (w/v). In other embodiments, the composition comprises about 0.05% (w/v) (e.g., hydroxyethylcellulose). The inventors have observed that compositions comprising high amounts of viscosity enhancing agents (e.g., hydroxyethylcellulose) result in clogging of the spray apparatus (e.g., the BD Accuspray™ device).

In one embodiment, the pharmaceutical composition of the present invention comprises the following components: tetracaine HCl, oxymetazoline HCl, anhydrous citric acid (for pH control), sodium hydroxide (for pH adjustment), benzyl alcohol, hydrochloric acid (for pH control), hydroxyethylcellulose, and purified water. In a particular embodiment, the pharmaceutical composition is for intranasal administration.

In a particular embodiment, the pharmaceutical composition of the present invention is the Table 1 formulation. In another embodiment, the Table 1 formulation is for intranasal administration.

In one embodiment, the Table 1 formulation has a pH of between about 4.0-6.5. In another embodiment the Table 1 formulation has a pH of between about 5.5-6.5. In another embodiment the Table 1 formulation has a pH of about 6.0 to about 6.5.

The pharmaceutical compositions of the present invention may be administered in several forms. Examples of suitable formulations include, but are not limited to, solutions, sprays, suspensions, lotions, gels, creams, foams, oils, emulsions, ointments, powders (such as $CaCO_3$ containing powders), lyophilized powders, or suppositories.

One of skill in the art will appreciate that the type of formulation used will depend on, for example, the amount of active ingredient to be administered and the target body part, organ or tissue.

Suitable lotion or cream formulations may comprise, for example, mineral oil, dimethyl sulfoxide (DMSO), sorbitan monostearate, polysorbate 60, cetyl esters wax, cetearyl alcohol, 2-octyldodecanol, benzyl alcohol, or combinations thereof.

Suitable gel formulations may comprise, for example, modified celluloses (e.g., hydroxypropyl cellulose and hydroxyethyl cellulose), carbopol homopolymers and copolymers, solvents such as diglycol monoethyl ether, alkylene glycols (e.g., propylene glycol), dimethyl isosorbide, alcohols (e.g., isopropyl alcohol and ethanol), isopropyl myristate, ethyl acetate, $C_{12}$-$C_{15}$ alkyl benzoates, mineral oil, squalane, cyclomethicone, capric/caprylic triglycerides, or combinations thereof.

Suitable foam compositions may comprise, for example, an emulsion and a gaseous propellant. Examples of gaseous propellants include, but are not limited to, hydrofluoroalkanes (HFAs) such as 1,1,1,2-tetrafluoroethane (HFA 134a) and 1,1,1,2,3,3,3-heptafluoropropane (HFA 227).

Suitable oil formulations may comprise, for example, natural and synthetic oils, fats, fatty acids, lecithins, triglycerides, or combinations thereof.

Suitable ointment formulations may comprise, for example, hydrocarbon bases (e.g., petrolatum, white petrolatum, yellow ointment, and mineral oil), absorption bases (e.g., hydrophilic petrolatum, anhydrous lanolin, lanolin, and cold cream), water-removable bases (e.g., hydrophilic ointment), water-soluble bases (e.g., polyethylene glycol ointments), propylene glycol, polyoxyethylene, polyoxypropylene, emulsifying wax, or combinations thereof.

In other embodiments, the pharmaceutical compositions optionally comprise pharmaceutically acceptable excipients. Examples of pharmaceutically acceptable excipients include, but are not limited to, preservatives, surfactants, stabilizing agents, emulsifiers, antibacterial agents, buffering agents and viscosity modifying agents. Specific examples of such excipients are discussed above.

Examples of emulsifiers include, but are not limited to, acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine and xanthan gum.

Methods of Anesthetizing Tissue

In one aspect, the present invention provides a method of anesthetizing at least a portion of a body part, organ, or tissue by administering a pharmaceutical composition of the invention. In some embodiments, the pharmaceutical composition is topically administered to the target body part, organ, or tissue. In some embodiments, the pharmaceutical composition is rubbed, sprayed, or spread on to the target body part, organ, or tissue. In some embodiments the pharmaceutical composition and/or target tissue are chilled before administration. In other embodiments the pharmaceutical composition and/or target tissue are heated before administration. In other embodiments, the pharmaceutical composition is administered by nebulization or injection. In yet other embodiments, the pharmaceutical composition is administered viz ionophoresis or ultrasound (typically at greater than 20,000 cycles/second).

Any delivery device may be used to apply the pharmaceutical composition to the body part, organ, or tissue. Examples of suitable delivery devices include, but are not limited to squeeze bottles, syringes, pneumatically pressurized devices, pump sprayers, positive pressure nebulizers and the like. In some embodiments, the device used is pre-filled with a pharmaceutical composition of the present invention.

In some embodiments, the invention provides a method for anesthetizing at least a portion of a patient's maxillary dental arch (and pain fibers external to the dental arch) in a subject comprising selectively delivering into the nasal cavity of the subject a pharmaceutical composition of the invention, wherein at least a portion of the pharmaceutical composition is absorbed by nasal tissue located at the rear of the nasal cavity in the vicinity of the sphenopalatine ganglion and, consequently, the maxillary nerve (and/or structures that communicate with the maxillary nerve), thereby anesthetizing at least a portion of the maxillary dental arch (and pain fibers outside but around the maxillary arch of the subject) of the subject. In some embodiments, the pharmaceutical compositions is delivered into the nasal sinuses and/or rear of the nasal cavity of the subject. In some embodiments, the maxillary dental arch is anesthetized without producing facial numbness of the eye, surface of the nose, cheeks or lips. In some embodiments, the tissues around the maxilla (e.g., mucosal tissue such as gums) are also anesthetized. In some embodiments, the pharmaceutical composition is delivered by nebulization or spraying. In some embodiments, the pharmaceutical composition is delivered to the nasal sinuses such as the maxillary sinus. In other embodiments, the pharmaceutical composition is delivered to the anterior dental plexus, extensions of the middle superior nerve, the posterior superior alveolar nerve, the nociceptors of the facial and buccal nerve, and/or the sphenopalatine (pterygopalatine) ganglion. In some embodiments, the pharmaceutical composition is also delivered to parts of the trigeminal ganglion. In other embodiments, the delivered spray is a stream or a plume.

In order to anesthetize the maxillary dental arch, the pharmaceutical composition must be administered to the tissue located at the extreme rear upper end of the nasal cavity such that the composition is absorbed in the region of the maxillary nerve and the pterygopalatine ganglion. The maxillary nerve as used herein refers to region of the nasal cavity where the posterior, middle and anterior superior alveolar nerves collect. These nerves are responsible for the initial transmission of transmitting pain, temperature and pressure impulses generated by the nerves of the maxillary dentition and surrounding maxillary bone. After the impulses pass through the maxillary nerve and the main trunk of the trigeminal nerve, they are transmitted to the brain for processing and recognition.

Any delivery device may be used in the methods of the present invention. Examples of delivery devices suitable for intranasal administration include, but are not limited to squeeze bottles, syringes, pneumatically pressurized devices, pump sprayers, positive pressure nebulizers and the like. In some embodiments, the device used is pre-filled with a pharmaceutical composition of the present invention. In another embodiment, the device used is a BD Accuspray™ device.

In some embodiments, the method comprises spraying the pharmaceutical composition 1-5 times into each of the nostrils of the subject. In other embodiments, the method comprises spraying the pharmaceutical composition 3 times into each of the nostrils of the subject.

Without being bound by any particular theory, it is believed that the each spraying may play a unique role in the onset of the anesthetic effect. For example, in embodiments wherein the pharmaceutical composition is delivered in 3 sprays, it is believed that the first spray begins to neutralize nasal enzymatic pathways (e.g., esterases, cytochrome P450, aldehyde dehydrogenase), which may breakdown the delivered pharmaceutical composition. It is also believed that the first spray begins to paralyze the nasal cilia which may otherwise clear the composition to, for example, the pharynx. It is further believed that the composition delivered in the second and third sprays bring on the anesthetic effect.

In some embodiments, each of the sprays are administered within about 1-10 minutes of each other. For example, spray #1 may be administered, followed by an interval of about 1-10 minutes, after which spray #2 is administered, followed by an interval of about 1-10 minutes, after which spray #3 is administered, etc. In some embodiments, the interval between sprays is about 1-6 minutes. In some embodiments, the interval between sprays is about 2-6 minutes. In other embodiments, the interval between sprays is about 3-5 minutes. In yet other embodiments, the interval between sprays is about 4 minutes.

The pharmaceutical compositions of the present invention are delivered to the maxillary sinus and the anterior dental plexus, as well as extensions of the middle superior alveolar nerve and sphenopalatine ganglion. Further, the pharmaceutical compositions of the present invention anesthetize at least a portion of the branches of the maxillary nerve and the pterygopalatine ganglion. In some embodiments, the pharmaceutical composition is also delivered to parts of the trigeminal ganglion (e.g., V2-V3 of the trigeminal ganglion). Depending on the extent of anesthetization, it is possible to anesthetize part or all of the surrounding tissues of the maxillary arch.

In embodiments where the method comprises spraying the pharmaceutical composition into the subject's nose, it has been found that the angle of spraying aids in targeting the formulation to the relevant portions of the nasal cavity described above. For example, where the pharmaceutical composition is delivered in 3 sprays, the following procedure may be used: For the first spray, the tip of the spray device can be positioned at an angle of about 35 to 45 degrees from the horizontal plane while the subject looks straight ahead. For the second spray, the tip of the spray device can be positioned at an angle of about −10 to +5 degrees from the horizontal plane while the subject looks straight ahead. The third spray can be delivered in the same fashion as the first spray. In some embodiments, the tip of the spray device can be positioned at an angle of about 42 degrees from the horizontal plane for the first and third sprays, and can be positioned at an angle of about zero degrees for the second spray. In other embodiments, the tip of the spray device is positioned approximately 0-2 mm inside the nose during sprayings.

In some embodiments, the targeting of specific teeth is desired. Thus, further refinements in the positioning of the spray device, in addition to those described above, may be employed. Without being bound by the following techniques, it is believed that the following modes of administration may also be employed. To target the anterior teeth (i.e., teeth 6-11), the spray device is angled about 0 to 15 degrees toward the midsagittal plane. To target the bicuspids (i.e., teeth 4, 5, 12, and 13), the spray device is angled about 5 degrees away to about 5 degrees toward the midsagittal plane. To target the posterior teeth (i.e., the molars or teeth 1-3 and 14-16), the spray device is angled about 0 to 10 degrees away from midsagittal plane. In other embodiments, the spray device is angled about 5 to 10 degrees toward the midsagittal plane for the anterior teeth, about parallel to the midsagittal plane for the bicuspids, and about 5 degrees away from midsagittal plane for the posterior teeth.

Tooth targeting may be further refined by varying the depth at which the spray device is placed within the nostril. For example, when spraying, the spray device can be placed about 2-3 mm within the nostril to target the anterior teeth, about 5 mm within the nostril to target the bicuspids, and about 7-9 mm to target the posterior teeth.

In some embodiments, a known (e.g., metered) amount of tetracaine is delivered into the nasal cavity of the subject. In other embodiments, the known (e.g., metered) amount of tetracaine is delivered into the nasal sinuses and/or rear of the nasal cavity of the subject. Typically, the amount of tetracaine delivered to the nasal sinuses and/or rear of the nasal cavity of the subject is about 12-50 mg of tetracaine. In some embodiments, about 15-24 mg of tetracaine is delivered into the nasal sinuses and/or rear of the nasal cavity of the subject. In some embodiments, about 15-20 mg of tetracaine is delivered into the nasal sinuses and/or rear of the nasal cavity of the subject. In some embodiments, the composition comprises about 2.0-5.0% (w/v) tetracaine. In some embodiments, the composition comprises about 2.25-4.75% (w/v) tetracaine. In other embodiments, the composition comprises about 2.5-4.0% (w/v) tetracaine. In yet other embodiments, a composition comprising about 2.5-3.5% (w/v) tetracaine is used. In a particular embodiment, the composition comprises about 3% (w/v) tetracaine. The inventors have observed that compositions comprising 2% tetracaine do not result in pulpal anesthesia, possibly due to insufficient amounts of tetracaine. The inventors also observed that compositions comprising 4% or more tetracaine were not as effective in inducing pulpal anesthesia.

In some embodiments, the particle size of the pharmaceutical composition delivered to the nasal sinuses and/or rear of the nasal cavity is about 5-50 microns. In other embodiments, the particle size of the pharmaceutical composition is about 10-20 microns. In some embodiments, the pharmaceutical composition is delivered in a manner such that at least 50% of the particles are at least about 10 microns or larger. In other embodiments, the pharmaceutical composition is delivered in a manner such that at least 65% of the particles are at least about 10 microns or larger. In other embodiments, the pharmaceutical composition is delivered in a manner such that at least 85% of the particles are at least about 10 microns or larger. In yet other embodiments, the pharmaceutical composition is delivered in a manner such that at least 90% of the particles are at least about 10 microns or larger. In further embodiments, the pharmaceutical composition is delivered in a manner such that at least 95% of the particles are at least about 10 microns or larger.

These and other embodiments of the invention may be further illustrated in the following non-limiting Examples.

EXAMPLES

Example 1

Identification of Effective and Safe Dosage of Tetracaine HCl Solution

The purpose of this study was to identify an effective and safe dosage of an intranasally administered tetracaine hydrochloride solution for obtaining anesthesia of the maxillary dentition. Healthy human volunteers were administered a dose of tetracaine HCl delivered as a nasal spray using a BD Accuspray™ device. The administration of the local anesthetic varied by total dose, concentration, and volume, and it included single doses in a single nostril, split doses in the same nostril, and divided doses in both nostrils. Different techniques regarding direction of spray were also investigated.

The efficacy of tetracaine hydrochloride in 80 subjects was measured by monitoring pain levels via electric pulp testing (EPT). EPT testing was accomplished by passing a current through the tooth to be tested wherein the lowest level of current is a "0" and the highest level of current is an "80." Subjects are exposed to an increasing amount of current (starting at 0 and ramping up to 80). If any pain was felt by the subject, the test was stopped and the EPT reading was recorded. A composition was considered successful at anesthetizing a tooth when, upon administration, the subject did not report any tooth pain up to a reading of 80.

Subjects received tetracaine doses between 4 and 16 mg. Nasal administration of tetracaine HCl did not result in maxillary arch anesthesia, as indicated by an EPT score of 80, in any of the subjects tested.

Example 2

Dose-Ranging Study of Tetracaine Hydrochloride with Oxymetazoline Hydrochloride for Anesthetizing Maxillary Teeth The purpose of this study, was to identify an effective and safe dosage of tetracaine hydrochloride with oxymetazoline HCl when administered by nasal spray for anesthesia of the maxillary teeth. Two formulations were administered to human patients using a BD Accuspray™ device—one with 3% tetracaine and 0.05% oxymetazoline; and another with 4% tetracaine and 0.05% oxymetazoline.

In all cases, the initial spray of the formulation was administered at a spray device angle of approximately zero degrees from the horizontal plane with the tip placed 0-2 cm inside the nostril with the subject looking straight ahead. For doses requiring more than one spray, the exact procedure set forth above was followed except the spray angle was changed to approximately 42 degrees. The efficacy of the formulation was measured by monitoring pain levels via electric pulp testing (EPT).

Three dosing regimes consisting of varying amounts of tetracaine HCl:oxymetazoline were evaluated: a) 12:0.2; b) 16:0.2; and c) 18:0.3 mg of tetracaine HCl:oxymetazoline HCl. Of the teeth tested, 60% in group a), 22% in group b), and 73% in group c) obtained pulpal anesthesia (defined as having at least one test with no sensation in the tooth at maximum EPT stimulation, i.e., a reading of 80 on the pulp tester). Further, 60% of subjects in group c) exhibited profound anesthesia (defined as having pulpal anesthesia beginning within 30 minutes after drug administration and continuing for at least 20 minutes in the first hour of testing on two of the three teeth tested).

Example 3

Packaging of the Table 1 Formulation

Batches of tetracaine HCl plus oxymetazoline HCl nasal spray were packaged into 0.5 ml BD Accuspray™ syringe systems with a 0.1 ml fill. Microbial Limits Testing (MLT) and chemistry testing were performed on the packaged syringes. As the formulation is light, and air/oxygen sensitive, contact with light and oxygen was minimized. Nitrogen was used to blanket bulk surface during processing, holding and filling.

Example 4

Evaluation of Particle Size of Table 1 Formulation Delivered with BD Accuspray™

The average droplet size of the Table 1 formulation, when dispensed with the BD Accuspray™ device, was evaluated. Droplet size was evaluated at distances of 3 cm and 6 cm from the device tip. The data from these experiments is summarized below in Table 2. As demonstrated by the data, on average, less than 1% of the droplets dispensed were less than 10 microns in diameter.

TABLE 2

Results of Particle Size Testing

| Distance From Device Tip | Average Percent of Particles <10 μm In Diameter* |
|---|---|
| 3 cm | 0.97% |
| 6 cm | 0.85% |

*Average of 10 runs

Example 5

Evaluation of Table 1 Formulation for Anesthetizing Maxillary Teeth in Healthy Subjects The Table 1 formulation was evaluated to determine if it: a) provided anesthesia of the maxillary teeth sufficient for the performance of dental procedures, and provided anesthesia of soft tissue; and b) was safe and tolerable compared to a sham nasal spray of isotonic saline in the BD Accuspray™ device, an active control injection of 2% lidocaine hydrochloride dental local anesthetic infiltration injection, and a sham injection.

Test Subjects

A total of 45 human subjects (30 receiving the Table 1 formulation, and 15 receiving Lidocaine) were enrolled in an active-controlled study. All subjects required an operative restorative procedure on a single maxillary tooth, other than a maxillary second or third molar, with treatment time that not expected to exceed 60 minutes.

Procedures

A schedule of the procedures is presented in Table 3.

TABLE 3

Schedule of Procedures

| | | |
|---|---|---|
| 0 min | | Administer first dose of nasal spray and perform injection (or sham injection), followed by sips of water |
| 4 min | | Administer second dose of nasal spray, followed by sips of water |
| 8 min | | Administer third dose of nasal spray, followed by sips of water |
| 15 min | | Begin dental procedure |
| 20 min* | | Soft Tissue Assessment, VAS |
| 30 min | | Soft Tissue Assessment |
| 40 min | | Soft Tissue Assessment |
| 50 min | | Soft Tissue Assessment |
| 60 min** | | Global VAS, Soft Tissue Assessment |
| 1 hr | 20 min | Soft Tissue Assessment |
| 1 hr | 40 min | Soft Tissue Assessment |
| 2 hr | | Soft Tissue Assessment |

*If subject is not sufficiently anesthetized to proceed with the dental procedure at 15 minutes, start at 20 minutes, immediately after Vital Signs and VAS
**VAS will be performed at the end of the dental procedure, regardless of the timepoint.
Abbreviations:
VAS = Visual Analog Scale Overview of Procedure Subjects were randomly assigned a treatment group and treatment order. The order of active drug administration (intranasal versus injection) was also random. Assessment of soft tissue anesthesia was made prior to dosing, and at 20, 30, 40, 60, 80, 100, and 120 minutes after dosing. At 0 min, either a) a single intraoral injection of lidocaine with epinephrine and sham nasal spray of isotonic saline was given; or b) a sham injection (depending on randomization group) and administration of a spray of the Table 1 formulation was administered. Additional doses of nasal spray were administered at 4 and 8 minutes. Subjects sipped approximately 2 oz of water following each active or placebo nasal spray dose. The Heft-Parker visual analog scale (VAS) was administered at 15 and 20 minutes after start of dosing. Dental treatment commenced 4 minutes after the last dose was given. If patients reported pain, the dental treatment did not commence until the 20 minute mark and an additional VAS test was given. Vital signs (heart rate, blood pressures, pulse oximetry) were taken before dosing, 15 minutes after the start of dosing, and at 20, 30, 40, 50, 60, and 120 minutes after the start of dosing. Global efficacy assessments was made at the end of treatment.

Test Product(s), Dose, and Mode of Administration

The Table 1 formulation was delivered in a BD Accuspray® mono-dose nasal spray device with backstop (BD Medical-Pharmaceutical Systems, Franklin Lakes, N.J.). Dose delivery was controlled by the solution concentration and volume contained in each syringe. All units were filled to deliver 0.1 mL. A total of six sprays (three in each nostril) of the Table 1 formulation were administered, with four minutes between each nasal spray dose. The total dosing period spanned 8 minutes. The total dosage of the Table 1 formulation was 18 mg tetracaine and 0.3 mg oxymetazoline.

The sham nasal spray consisted of isotonic saline solution.

The active control injection consisted of 2% lidocaine HCl and epinephrine (1:100,000) USP (LolliCaine single-use applicators, Centrix). The injection was performed with a 30-gauge short needle inserted submucosally approximating the apex of the tooth to be treated. The dosage of the 2% lidocaine hydrochloride with 1:100,000 epinephrine injection consisted of one-half cartridge (0.9 mL) delivered over 30 seconds for the treatment of anterior or premolar teeth, and one cartridge (1.8 mL) delivered over 60 seconds for the treatment of a first molar.

The sham injection consisted of a dental syringe and lidocaine with epinephrine cartridge but with the cap left on a 30-gauge short needle tip. The needle cap was held against the mucosa in the proper position for the injection for 30 seconds for anterior and premolar teeth and 60 seconds for molar teeth. No solution was injected.

A small amount of 20% benzocaine gel was used on all subjects to provide topical anesthesia 1 minute before active or sham needle insertions.

The rescue therapy consisted of 4% articaine hydrochloride with 1:100,000 epinephrine injection (Septocaine, Septodont).

The Dosing Algorithm consisted of:
Administration of topical benzocaine gel 1 min before dosing with sham or active injection
Administration dose of injection or initial dose of nasal spray (T=0 min)
If initial dose was nasal spray, at 4 min, administration of a second dose of nasal spray
If initial dose was nasal spray, at 8 min, administration of a third dose of nasal spray
At 15 min, proceeding with dental treatment Subjects sipped approximately 2 oz of water one minute after each dose of nasal spray (i.e., at approximately 2 and 5 min, and at 10 min). When subjects reported pain at the onset of dental treatment, the dentist stopped treatment and waited five minutes (to a total of 20 minutes post start of dosing). Subjects who continued to report pain at resumption of dental treatment were considered "treatment failures" and were given rescue therapy.

Administration of Treatment

For each spray, the subject was sitting up with their chin slightly down. During each spray, the subject was instructed to hold his/her breath. After each spray the subject was asked to gently sniff.

For the first spray, the tip of the spray device was positioned approximately 0-2 cm inside the nose at an angle of 0 degrees from the horizontal plane; the subject looked straight ahead. For the second and third sprays, the tip of the spray device was positioned approximately 0-2 cm inside the nose at an angle of 42 degrees from the horizontal plane as illustrated in the diagram below; again the subject looked straight ahead.

Assessment of Efficacy

In order to assess soft tissue anesthesia, a dental professional used a pressure sensitive mechanical probe (i.e., Rotadent®) and tested the following areas for soft tissue anesthesia: distal to the apex of the tooth in the position of the maxillary first premolar at the deepest point in the buccal vestibule; apical to the maxillary lateral incisor at the deepest point in the labial vestibule; incisive papilla; and at the confluence of the alveolar process and hard palate medial to the maxillary second premolar (near the greater palatine foramen). For each site tested, the subject was asked if they felt pain. Efficacy of the formulation was determined by the ability to accomplish the dental procedure without the need for rescue drug.

Results

Of the 25 patients that received the Table 1 formulation and successfully completed the study, 22 fully completed the procedures/testing without the need for rescue therapy for a success rate of ~88%. Of the 15 patients that received injected lidocaine and successfully completed the study, 14 fully completed the procedures/testing without the need for rescue therapy for a success rate of ~93%. Accordingly, there is no statistical difference between the intranasal Table 1 formulation and the control, locally injected lidocaine formulation with respect to their ability to anesthetize the tested teeth. Thus, the Table 1 formulation provides an effective means of anesthetizing teeth without need for painful injection procedures.

Example 6

Evaluation of Effect of Time Between Intranasal Administration of Table 1 Formulation Sprays The effect of the interval time between sprays was evaluated. In particular, interval times of about 1, 2, 3, 4, and beyond 4 minutes were evaluated. It was observed that shorter interval times between spray administrations (i.e., interval times of about 1, 2, or 3 minutes between sprays) resulted in faster onset of the anesthetic affect, but a shorter duration of the anesthetic effect, when compared to an interval time of about 4 minutes. It was also observed that waiting more than 4 minutes between spray administrations did not affect the time of anesthetic onset, but resulted in a short duration of anesthetic affect.

What is claimed is:
1. A pharmaceutical composition comprising:
   a) 2.5-3.5% (w/v) tetracaine, or a pharmaceutically acceptable salt thereof;
   b) a vasoconstrictor; and
   c) a pharmaceutically acceptable carrier.
2. The pharmaceutical composition according to claim 1, wherein said pharmaceutical composition is for intranasal administration.
3. The pharmaceutical composition according to claim 2, wherein said composition comprises about 3% (w/v) tetracaine.
4. The pharmaceutical composition according to claim 2, wherein said vasoconstrictor is selected from the group consisting of: indirect $\alpha_1$-adrenergic agonists; calcium channel blockers; meperidine; imidazole drugs; $\alpha_2$-adrenergic agonists; imidazoline ($I_1$) ligands; direct $\alpha_2$-adrenergic agonists; substance P blockers/reducers; I-menthol; icilin; glutamate receptor inhibitors; and pharmaceutically acceptable salts thereof.
5. The pharmaceutical composition according to claim 4, wherein said vasoconstrictor is oxymetazoline, or a pharmaceutically acceptable salt thereof.
6. The pharmaceutical composition according to claim 5, wherein said oxyrnetazoline is oxymetazoline salt.
7. The pharmaceutical composition according to claim 6, wherein said composition comprises about 0.01-1.0% (w/v) oxymetazoline HCl.
8. The pharmaceutical composition according to claim 7, wherein said composition comprises about 0.05% (w/v) oxymetazoline HCl.
9. The pharmaceutical composition according to claim 2, wherein said composition further comprises a preservative.
10. The pharmaceutical composition according to claim 9, wherein said preservative is selected from the list consisting of: sugar alcohols, ethanol, benzyl alcohol, isopropanol, cresol, chlorocresol, and phenol.
11. The pharmaceutical composition according to claim 10, wherein said preservative is benzyl alcohol.
12. The pharmaceutical composition according to claim 11, wherein said composition comprises about 0.5-2.0% (w/v) benzyl alcohol.
13. The pharmaceutical composition according to claim 12, wherein said composition comprises about 0.9% (w/v) benzyl alcohol.
14. The pharmaceutical composition according to claim 2, wherein said composition further comprises a viscosity enhancing agent.
15. The pharmaceutical composition according to claim 14, wherein said viscosity enhancing agent is selected from the list consisting of: methylcellulose, hydroxyethylcellulose, hydroxypropylmethylcellulose and smart hydrogel.
16. The pharmaceutical composition according to claim 15, wherein said viscosity enhancing agent is hydroxyethylcellulose.
17. The pharmaceutical composition according to claim 16, wherein said composition comprises about 0.01-1.0% (w/v) hydroxyethylcellulose.

18. The pharmaceutical composition according to claim 17, wherein said composition comprises about 0.05% (w/v) hydroxyethylcellulose.

19. The pharmaceutical composition according to claim 2, wherein said pharmaceutically acceptable carrier is water, sugar alcohol, or alcohol (e.g., ethanol).

20. The pharmaceutical composition according to claim 19, wherein said pharmaceutically acceptable carrier is water.

21. The pharmaceutical composition according to claim 2, wherein said composition has a pH of 4.0-6.5.

22. The pharmaceutical composition according to claim 2, wherein said composition has a pH of 5.5~6.5.

23. The pharmaceutical composition according to claim 2, wherein said composition further comprises a preservative and a viscosity enhancing agent.

24. The pharmaceutical composition according to claim 2, wherein said composition comprises:

| Ingredient | Formulation (% w/v) |
| --- | --- |
| Tetracaine hydrochloride, USP | 3.00 |
| Oxymetazoline hydrochloride, USP | 0.05 |
| Citric acid anhydrous, USP | 1.00 |
| Sodium hydroxide, NF | q.s. |
| Benzyl alcohol, NT | 0.90 |
| Hydrochloric acid, NF | q.s. |
| Hydroxyethylcellulose, NF (5000 cps) | 0.05 |
| Purified water, USP | q.s. to 100%. |

25. A method for anesthetizing at least a portion of a patient's maxillary dental arch in a subject comprising selectively delivering into the nasal sinuses or rear of the nasal cavity of the subject a pharmaceutical composition according to claim 2, wherein at least a portion of the pharmaceutical composition is absorbed by nasal tissue located at the rear of the nasal cavity in the vicinity of the maxillary sinus.

26. The method according to claim 25, wherein at least a portion of the pharmaceutical composition is absorbed by nasal tissue located at the rear of the nasal cavity in the vicinity of the anterior dental plexus, extensions of the middle superior nerve, the posterior superior alveolar nerve, the nociceptors of the facial and buccal nerve, or the sphenopalatine (pterygopalatine) ganglion.

27. The method according to claim 26, wherein said pharmaceutical composition is delivered by nebulization or spraying.

28. The method according to claim 27, wherein said delivered spray is a stream or a plume.

29. The method according to claim 28, wherein the selective delivery into the nasal sinuses or rear of the nasal cavity comprises spraying said pharmaceutical composition 1-5 times into each of the nostrils of said subject.

30. The method according to claim 29, wherein said selective delivery into the nasal sinuses or rear of the nasal cavity comprises spraying said pharmaceutical composition 3 times into each of the nostrils of said subject.

31. The method according to claim 30, wherein each of the 3 sprays into each of the nostrils of said subject are separated by an interval of 4 minutes.

32. The method according to claim 26, wherein about 12-50 mg of tetracaine is delivered into the nasal sinuses or rear of the nasal cavity of said subject.

33. The method according to claim 32, wherein about 15~24 mg of tetracaine is delivered into the nasal sinuses or rear of the nasal cavity of said subject.

34. The method according to claim 26, wherein the particle size of said pharmaceutical composition that is delivered to the nasal sinuses or rear of the nasal cavity is about 5-50 microns.

35. The method according to claim 34, wherein the particle size of said pharmaceutical composition is about 10-20 microns.

36. The method according to claim 35, wherein the particle size of said pharmaceutical composition is about 10 microns or larger.

37. The method according to claim 36, wherein at least 85% of the particles of the pharmaceutical composition are about 10 microns or larger.

38. A method for anesthetizing at least a portion of a body part, organ, or tissue by delivering a pharmaceutical composition according to claim 2.

39. The method according to claim 38, wherein said tissue is epithelial tissue.

40. The method according to claim 39, wherein said tissue is mucosal tissue.

41. A device for delivery of a pharmaceutical composition, wherein said device comprises a pharmaceutical composition according to claim 2.

42. The device according to claim 41, wherein said device is for intranasal delivery of a pharmaceutical composition according to claim 2.

43. The device according to claim 42, wherein said device is capable of delivering said pharmaceutical composition to the nasal tissue located at the rear of the nasal cavity in the vicinity of the sphenopalatine (pterygopalatine) ganglion and maxillary nerve.

44. The device according to claim 42, wherein said device is pre-filled with a pharmaceutical composition according to claim 2.

45. The device according to any one of claims 42-44, wherein said device is a spray device.

* * * * *

UNITED STATES PATENT AND TRADEMARK OFFICE
CERTIFICATE OF CORRECTION

PATENT NO.         : 8,580,282 B2                                   Page 1 of 1
APPLICATION NO.    : 13/262704
DATED              : November 12, 2013
INVENTOR(S)        : Mark David Kollar It is certified that error appears in the above-identified patent and that said Letters Patent is hereby corrected as shown below:

IN THE SPECIFICATION:

At column 1, lines 42 and 43, please remove "but the of local anesthetics produce fear, pain and an increase in blood pressure,".

At column 8, line 15, please change "thereof In" to -- thereof. In --.

IN THE CLAIMS:

At column 18, claim 6, line 34, please change "oxymetazoline salt" to -- oxymetazoline HCl salt --.

Signed and Sealed this
Seventeenth Day of June, 2014

Michelle K. Lee
*Deputy Director of the United States Patent and Trademark Office*